United States Patent
Gröppel et al.

(10) Patent No.: US 11,877,995 B2
(45) Date of Patent: Jan. 23, 2024

(54) COMPOUNDS AND DOSAGE REGIMEN FOR USE IN THE PREVENTION OR TREATMENT OF CHRONIC INFLAMMATORY AND/OR AUTOIMMUNE DISEASES

(71) Applicant: Immunic AG, Gräfelfing (DE)

(72) Inventors: Manfred Gröppel, Munich (DE); Daniel Vitt, Germering (DE); Hella Kohlhof, Munich (DE); Andreas Mühler, Munich (DE)

(73) Assignee: IMMUNIC AG, Grafelfing (DE)

(*) Notice: Subject to any disclaimer, the term of this patent is extended or adjusted under 35 U.S.C. 154(b) by 0 days.

(21) Appl. No.: 17/992,162

(22) Filed: Nov. 22, 2022

(65) Prior Publication Data

US 2023/0116729 A1 Apr. 13, 2023

Related U.S. Application Data

(62) Division of application No. 16/766,531, filed as application No. PCT/EP2018/082272 on Nov. 22, 2018, now abandoned.

(30) Foreign Application Priority Data

Nov. 23, 2017 (EP) .................................... 17203407

(51) Int. Cl.
*A61K 31/196* (2006.01)
*A61P 19/06* (2006.01)

(52) U.S. Cl.
CPC ............ *A61K 31/196* (2013.01); *A61P 19/06* (2018.01)

(58) Field of Classification Search
CPC .............................. A61K 31/196; A61P 19/06
See application file for complete search history.

(56) References Cited

U.S. PATENT DOCUMENTS

| | | | |
|---|---|---|---|
| 7,423,057 | B2 | 9/2008 | Leban et al. |
| 8,653,138 | B2 | 2/2014 | Ammendola et al. |
| 2012/0029034 | A1 | 2/2012 | Ammendola |
| 2016/0287549 | A1 | 10/2016 | Dodge |

FOREIGN PATENT DOCUMENTS

| | | |
|---|---|---|
| CA | 2930429 A1 | 5/2016 |
| EP | 2093214 A1 | 8/2009 |
| WO | 12001148 A1 | 1/2012 |

OTHER PUBLICATIONS

Herrlinger K R et al: "Efficacy, safety and tolerability of vidofludimus in patients with inflammatory bowel disease: The Entrance study", Journal of Crohn's and Colitis, vol. 7, No. 8, Sep. 1, 2013 (Sep. 1, 2013), pp. 636-643, XP028595631, ISSN: 1873-9946.

International Search Report WO2018EP82272 dated Mar. 7, 2019 (pp. 1-4).
Leban et. al. (Bioorganic and Medicinal Letters (2005) 15:4854-4857). (Year: 2005).
Drugs.com—Drug Dosage.
Musuamba FT et al Advanced Methods for Dose and Regimen Finding During Drug Development: Summary of the EMA/EFPIA Workshop on Dose Finding (London Dec. 4-5, 2014) pp. 418-429.
Fitzpatrick LR et al, "Vidofludimus Inhibits Colonic Interleukin-17 and Improves Hapten-Induced Colitis in Rats by a Unique Dual Mode of Action", The Journal of Pharmacology and Experimental Therapeutics, 2012, 342, 850-860, published online Aug. 14, 2012. DOI: 10.1124/jpet.112.192203.
Rusai K et al "Immunosuppression With 4SC-101, a Novel Inhibitor of Dihydroorotate Dehydrogenase, in a Rat Model of Renal Transplantation", Transplantation, 2012, 93, 1101-1107, published Jun. 15, 2012. DOI: 10.1097/TP.0b013e31824fd861.
Catana C et al, "Contribution of the IL-17/IL-23 axis to the pathogenesis of inflammatory bowel disease", World J Gastroenterol, 2015, 21(19), 5823-5830, published online May 21, 2015. DOI: 10.3748/wjg.v21.119.5823.
Hanke T et al, "Small molecules with anti-inflammatory properties in clinical development", Pharmacology & Therapeutics, 2016, 157, 163-187, published online Nov. 26, 2015. DOI: 10.1016/j.pharmthera.2015.11.011.
Fitzpatrick LR, "Inhibition of IL-17 as a Pharmacological Approach for IBD", International Reviews of Immunology, 2013, 32, 544-555, published online: Jul. 25, 2013, DOI: 10.3109/08830185.2013.821118.
Gómez-Gómez GJ et al, "Current stage in inflammatory bowel disease: What is next?", World J Gastroenterol 2015, 21(40), 11282-11303, published online: Oct. 28, 2015. DOI: 10.3748/wjg.v21.140.11282.

(Continued)

*Primary Examiner* — Marcos L Sznaidman
(74) *Attorney, Agent, or Firm* — Finnegan, Henderson, Farabow, Garrett & Dunner, LLP

(57) ABSTRACT

The present invention refers to a 2-({3-fluoro-3'-methoxy-[1,1'-biphenyl]-4-yl}carbamoyl)cyclopent-1-ene-1-carboxylic acid) according to formula (I)

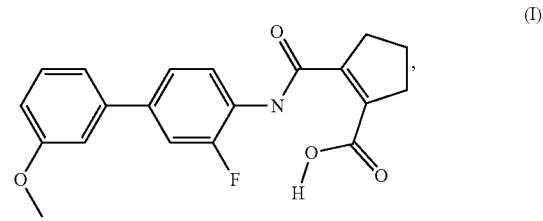

Figure 1:
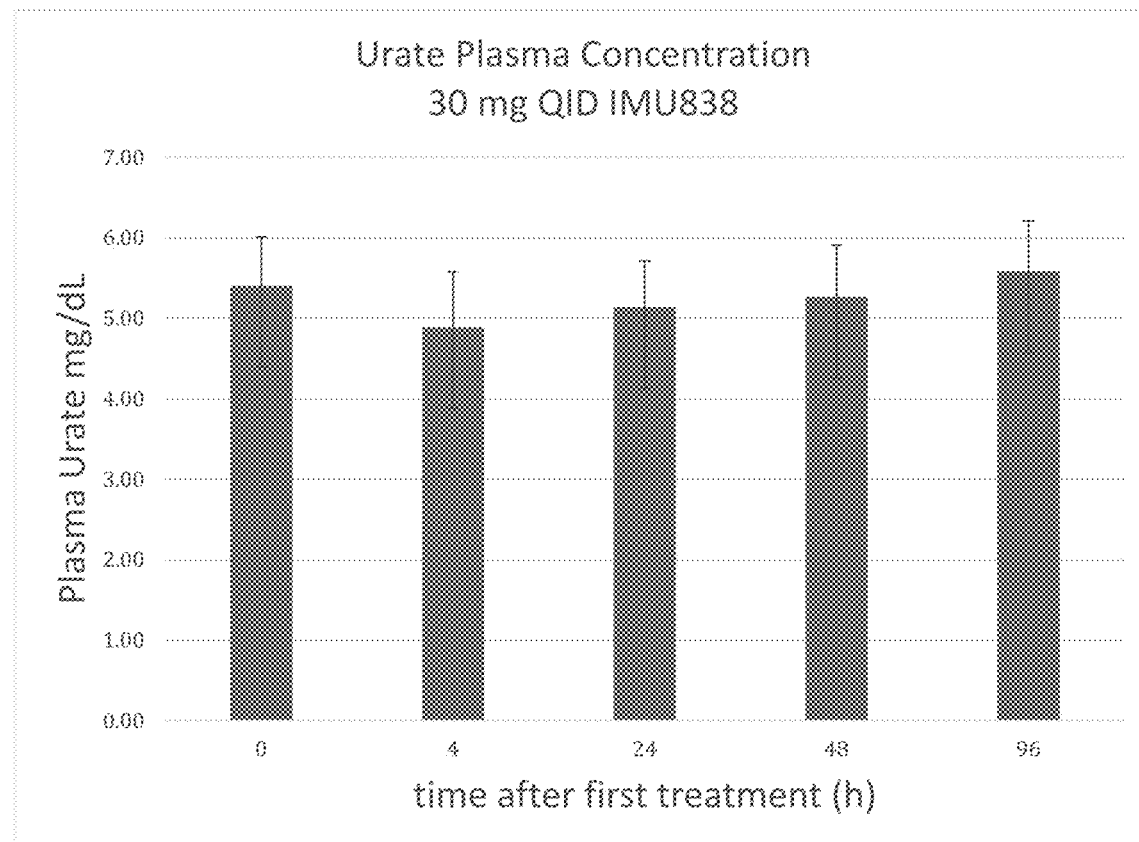

and a novel dosage regimen as well as their uses in the treatment of chronic inflammatory and/or autoimmune diseases. The said compound of formula (I) inhibits dihydroorotate dehydrogenase (DHODH), and is known for the treatment and prevention of diseases, in particular their use in diseases where there is an advantage in inhibiting dihydroorotate dehydrogenase (DHODH).

34 Claims, 2 Drawing Sheets

(56) References Cited

OTHER PUBLICATIONS

Fitzpatrick LR et al, "Vidofludimus Inhibits Colonic IL-17 and Improves Hapten-Induced Colitis in Rats by a Unique Dual Mode of Action", conference presentation at Digestive Disease Week, San Diego in May 19-22, 2012 (pp. 1-14).
Fitzpatrick LR et al, "Vidofludimus Inhibits Colonic IL-17 and Improves Hapten-Induced Colitis in Rats by a Unique Dual Mode of Action", Gastroenterology 2012, 142(5), Supplement 1, S-84, published May 2012. DOI: 10.1016/S0016-5085(12)60317-5.
Hamm S et al, "Vidofludimus induces p53-mediated apoptosis in activated T cells and inhibits IL-17A and IL-17F expression decoupled from lymphocyte proliferation", poster presentation at Digestive Disease Week, San Diego in May 19-22, 2012, Abstract No. Tu1875 (1 page).
Fitzpatrick LR et al, "Vidofludimus Inhibits IL-17 and Improves Hapten-Induced Colitis in Young Rats by a Unique Dual Mode of Action", poster presentation at 7th Congress of ECCO—Inflammatory Bowel Disease Feb. 17, 2012, Barcelona, Spain, Poster No. P012 (1 page).
"Kulkarni OP et al, ""4SC-101, A Novel Small Molecule Dihydroorotate Dehydrogenase Inhibitor, Suppresses SystemicLupus Erythematosus in MRL-(Fas)lpr Mice"", The American Journal of Pathology, 2010, 176(6), 2840-2847, published online: Apr. 22, 2010. DOI: 10.2353/ajpath.2010.091227".
Sierakowski S et al "Efficacy, Safety and Pharmacokinetics of Vidofludimus, a Novel Oral Immunomodulator, in Patients with Active Rheumatoid Arthritis on Methotrexate Background Therapy: The Component Study", poster presentation at American College of Rheumatology 2011, Nov. 4-10, Chicago, IL (USA), Abstract #18848 (1 page).
Kulkarni O et al, "Vidofludimus shows a superior profile compared to cyclophosphamide and MMF in an experimental systemic lupus erythematosus model", poster presentation at European League Against Rheumatism (EULAR) Congress, London, United Kingdom, May 25-28, 2011 (1 page).
"Fitzpatrick LR et al, ""Inhibition of IL-17 Release by the Novel Anti-Inflammatory Drug Vidofludimus Involves Attenuationof STAT3 and NF-kappa B Signaling Pathways in Murine Splenocytes and Hapten-Induced Colitis"", poster presentation at Digestive Disease Week 2011, Chicago, May 7-11, Abstract No. Tu1800" (1 page).
Herrlinger KR et al, "Efficacy, Safety and Tolerability of Vidofludimus in Patients with Inflammatory Bowel Disease: the Entrance Study", poster presentation at 6th Congress of ECCO—Inflammatory Bowel Disease Feb. 25, 2011, Dublin, Ireland, Poster No. P209 (1 page).
"Fitzpatrick LR et al, ""4SC-101, a Novel Immunosuppressive Drug, Inhibits IL-17 and Attenuates Colitis in Two Murine Models ofinflammatory Bowel Disease"" Inflamm Bowel Dis, 2011, 16(10), 1763-1777, published online: Mar. 22, 2010. DOI: 10.1002/lbd.21264".
Fitzpatrick LR et al, "A Novel Immunosuppressive Drug (4SC-101) Improves TNBS-Induced Colitis in Mice", poster presentation at Digestive Disease Week 2011, Chicago, May 7-11, Abstract No. M1658 (1 page).
Leban J et al, "SAR, species specificity, and cellular activity of cyclopentene dicarboxylic acid amides as DHODH inhibitors", Bioorg Med Chem Lett, 2005, 15(21), 4854-4857, published online Sep. 6, 2005. DOI: 10.1016/j.bmcl.2005.07.053.
Leban J et al, "Discovery of a novel series of DHODH inhibitors by a docking procedure and QSAR refinement", Bioorg Med Chem Lett. 2004, 14(1), 55-58, published online Dec. 2, 2003. DOI: 10.1016/j.bmcl.2003.10.021.
Baumgartner R et al, "Dual Binding Mode of a Novel Series of DHODH Inhibitors", J. Med. Chem. 2006, 49, 1239-1247, published online Jan. 26, 2006. DOI: 10.1021/jm0506975.
Fitzpatrick LR et al, "A Novel Immunosuppressive Drug (4SC-101) Improves TNBS-Induced Colitis in Mice", poster presentation at Digestive Disease Week 2009, Chicago, USA, May 28, 2009 (1 page).

Strobl S et al, "Vidofludimus, a New IL-17 and DHODH Inhibitor for Treatment of Inflammatory and Autoimmune Diseases", poster presentation at 14th International Symposium on Purine and Pyrimidine Metabolism in Man, Tokyo, Japan, Feb. 8-21, 2011 (1 page).
Herrlinger KR et al, "Efficacy, Safety and Tolerability of Vidofludimus in Patients with Inflammatory Bowel Disease: the Entrance Study", Digestive Disease Week, May 7-10, 2011, Chicago, IL (USA), Abstract #1034088 (1 page).
"Fitzpatrick LR et al, ""Novel Pharmacological Approaches for Inflammatory Bowel Disease: Targeting Key Intracellular Pathwaysand the IL-23/IL-17 Axis"", Int J Inflam, 2012, 389404. published online Mar. 15, 2012. DOI: 10.1155/2012/389404".
"Immunic, Inc. Announces 200 Patients Enrolled in Its Phase 2 CALVID-1 Trial of IMU-838 for the Treatment of Moderate COVID-19, Allowing for Main Phase 2 Efficacy Analysis to Proceed", press release, Immunic Inc, Nov. 2, 2020.
"Immunic, Inc. Announces Results From Interim Safety Analysis and Recruitment Update From Its Ongoing Phase 2 CALVID-1 Trial of IMU838 in Patients With Moderate COVID-19", press release, Immunic Inc, Sep. 28, 2020 (pp. 1-3).
"Immunic, Inc. Publishes Full Unblinded Clinical Data From Phase 2 EMPHASIS Trial of IMU-838 in Patients With Relapsing-Remitting Multiple Sclerosis and Announces Poster Presentation at the MSVirtual2020", press release, Immunic Inc, Sep. 11, 2020 (1 page).
"Immunic Therapeutics—IMU-838 Phase 2 Data EMPHASIS Trial in RRMS", presentation from Sep. 11, 2020 (pp. 1-6).
"Immunic, Inc. Reports Positive Top-line Data from Phase 2 Emphasis Trial of IMU-838 in Patients with Relapsing-Remitting Multiple Sclerosis", press release, Immunic Inc, Aug. 2, 2020 (pp. 1-9).
"Immunic Therapeutics IMU-838 Phase 2 Top-Line Data Emphasis Trial in RRMS", presentation from Aug. 3, 2020 (pp. 1-35).
"Immunic Therapeutics Inaugural R&D Day", presentation from Immunic Virtual R&D Day, May 19, 2020 (pp. 1-169) (pp. 1-19).
Fox R, "Multiple Sclerosis Treatment Landscape and Unmet Needs", presentation from Immunic Virtual R&D Day, May 19, 2020 (1-44).
"Immunic—"Developing Selective Oral DHODH Inhibitor IMU-838as COVID-19 Therapy"", presentation from Apr. 22, 2020 pp. 1-19.
Muehler A et al, "The DHODH Inhibitor IMU-838/Vidofludimus Calcium Shows a Superior Compound Profile as Compared to the Approved DHODH Inhibitor, Teriflunomide", poster presentation at the Congress of the European Committee for Treatment and Research in Multiple Sclerosis 2019, Sep. 11, 2019 (1 page).
Kohlhof H, "IMU-838 in Clinical Phase 2—New Selective Oral Treatment for IBD", presentation at GI Inflammatory Diseases Summit (GIIDS) in Boston, US, Jun. 24, 2019 (1 page).
Muehler A et al, "Vidofludimus calcium, a next generation DHODH inhibitor for the Treatment of relapsing-remitting multiple sclerosis", Multiple Sclerosis and Related Disorders , 2020, 43, 102129, published online May 5, 2020. DOI: 10.1016/j.msard.2020.102129.
Muehler A et al, "Safety, Tolerability and Pharmacokinetics of Vidofludimus calcium (IMU-838) After Single and Multiple Ascending Oral Doses in Healthy Male Subjects", European Journal of Drug Metabolism and Pharmacokinetics, 2020, 45(5), 557-573, published online May 2, 2020. DOI: 10.1007/s13318-020-00623-7.
Fox R et al, "Design, Rationale and Baseline Characteristics of the Randomized Double-blind Phase II Clinical Trial of Vidofludimus calcium (IMU-838) in Relapsing-Remitting Multiple Sclerosis (4558)", Neurology, 2020, 94 (15 Supplement), 4558, published online Apr. 14, 2020.
Muehler A et al, "The Selective Oral Immunomodulator Vidofludimus in Patients with Active Rheumatoid Arthritis: Safety Results from the Component Study", Drugs in R&D, 2019, 19(4), 351-366, published online Oct. 16, 2019. DOI: 10.1007/s40268-019-00286-z.
Marschall et al, "Assessment of drug candidates for broad-spectrum antiviral therapy targeting cellular pyrimidine biosynthesis", Antiviral Research, 2013, 100, 640-648, published online Oct. 20, 2013. DOI: 10.1016/j.antiviral.2013.10.003.
Fox et al, "Efficacy and safety of the selective oral DHODH modulator vidofludimus calcium (IMU-838) in relapsing-remitting multiple sclerosis: a randomized, placebo-controlled Phase 2 trial

(56) References Cited

OTHER PUBLICATIONS (EMPhASIS)", poster presentation at the 2021 Virtual AAN Annual Meeting, Apr. 17-22, 2021 (pp. 1-2).

Kohlhof H et al, "Preclinical Investigations of IMU-838, an Orally Available Small Molecule Inhibitor of Dihydroorotate Dehydrogenase for the Treatment of Inflammatory Bowel Disease" poster presentation at United European Gastroenterology Week (UEGW), Barcelona, Spain, Oct. 22, 2019 (1 page).

Kim Y et al, "Novel Dihydroorotate Dehydrogenase Inhibitors with Potent Interferon-Independent Antiviral Activity against Mammarenaviruses In Vitro", Viruses, 2020, 12, 821, published online Jul. 29, 2020. DOI: 10.3390/v12080821.

Hahn F et al, "IMU-838, a Developmental DHODH Inhibitor in Phase II for Autoimmune Disease, Shows Anti-SARS-CoV-2 and Broad-Spectrum Antiviral Efficacy In Vitro", Viruses, 2020, 12, 1394, published online Dec. 5, 2020. DOI: 10.3390/v12121394.

Hamm S et al, "Vidofludimus induces p53-mediated apoptosis in activated T cells and inhibits IL-17A and IL-17F expression decoupled from lymphocyte proliferation", poster presentation at 7th Congress of ECCO-IBD, Feb. 17, 2012, Poster No. P013 (1 page).

COMPOUNDS AND DOSAGE REGIMEN FOR USE IN THE PREVENTION OR TREATMENT OF CHRONIC INFLAMMATORY AND/OR AUTOIMMUNE DISEASES

The invention refers to a compound 2-({3-fluoro-3'-methoxy-[1,1'-biphenyl]-4-yl}carbamoyl)cyclopent-1-ene-1-carboxylic acid) according to formula (I), CAS-No 717824-30-1,

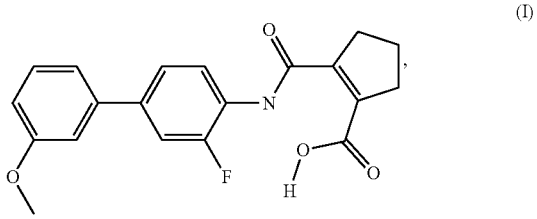 [SMILES: COc1cccc(-c2ccc(NC(=O)C3=C(C(=O)O)CCC3)c(F)c2)c1]

or salts thereof or solvates of the compound of formula (I) or the salts thereof and a novel dosage regimen as well as their uses in the prevention and/or treatment of diseases, specifically chronic inflammatory and/or autoimmune diseases.

The compound of formula (I) inhibits dihydroorotate dehydrogenase (DHODH), and is known for the treatment and prevention of diseases, in particular their use in diseases where there is an advantage in inhibiting dihydroorotate dehydrogenase (DHODH).

In the human body, DHODH catalyzes the synthesis of pyrimidines, which are in particular necessary for cellular metabolism. An inhibition of DHODH leads to block of transcription of sensitive genes in metabolically activated cells, whereas cells with normal metabolic activity obtain their required pyrimidine building blocks from the pyrimidine salvage pathway and show normal transcriptional activity. Disease relevant activated lymphocytes rely on de novo pyrimidine syntheses and react particularly sensitively to DHODH inhibition. Some substances that inhibit DHODH are important medicaments for its use in the treatment of chronic inflammatory and auto-immune diseases.

A novel class of compounds with an inhibitory effect on DHODH, in particular human DHODH, was found and described in EP 2 093 214 A1. Vidofludimus (CAS 717824-30-1) is the free acid of a compound according to formula (I) and is tested in clinical trials in human subjects. A higher dose of vidofludimus in the plasma has been shown to be beneficial for its use in therapeutic treatment of patients, particularly in chronic inflammatory and autoimmune disease, blocking DHODH by vidofludimus. Higher dose means e.g. doses higher than 50 µmol once daily application of vidofludimus in humans. However, doses of compounds of formula (I), e.g. higher than 200 µmol once daily application, sometimes lead to undesirable side effects such as an increased risk of increased red blood cell count (RBC) in the urine (hematuria).

At high vidofludimus doses (i.e. ≥70 mg/day or single doses of ≥210 mg) a decrease in blood uric acid levels and an increase in urine red blood cell count were observed, in very rare cases, presenting as symptomatic hematuria during the first 7 days of treatment. Laboratory findings were consistent with post-renal events and de novo precipitates in the urinary tract. However, no cases of symptomatic hematuria were seen at daily doses of 35 mg vidofludimus.

Increased RBC and hematuria has been associated with increased excretion of uric acid and may result from crystallization of uric acid or urate in the urinary tract. It is perceived that normally around 5-10% of all people have crystalline uric acid or urate in their urine [Pak, C. Y. C. The Journal of Urology 180, 813-819 (2008)]. An increased rate of hematuria is considered as unwanted side effects.

It was, thus, the object of the present invention to reduce or avoid side effects without substantially compromising the beneficial effect of the treatment. Surprisingly, a special dosage regimen was found and provided by the present invention that reduces or avoids side effects without substantially compromising the beneficial effect of the treatment of said patients in need of prevention and/or treatment and/or allow for higher dosing of compounds of formula (I) during its use in the prevention and/or treatment of patients with compounds of formula (I).

A side effect that may also be termed adverse effect is a harmful and undesired effect resulting from medication during its use in the prevention and/or treatment of a patient with the inventive compound (I). The inventors have observed that the e.g. hematuria may occur after dosing the inventive compound of formula (I) in a range from about 12 to about 168 hours after the start of the treatment with a first dose of 70 mg daily dose of vidofludimus or higher.

Evaluation of RBC in urine, known in the art such as urinalysis, should be based solely on findings from microscopic examination of urinary sediment and not from dipstick reading only [Grossfeld G D, et al., Am Pam Physician 2001; 63(6):1145-54]. Therefore, all conspicuous dipstick readings should be followed up by a microscopic examination of urinary sediment.

According to the embodiments of the present inventive dosage regimen, the occurrence and/or the extent of increased urate crystals and/or increased RBC in urine and/or hematuria is reduced or completely prevented.

The term "increased" versus "normal" extent of urate crystals and/or "increased RBC" versus "normal RBC" in urine refers to the value of the patient when not undergoing the inventive treatment. The evaluation of a normal extent of urate crystals and/or increased RBC in urine is within the ability of a correspondent physician.

Subject matter of the present invention is a compound that is 2-({3-fluoro-3'-methoxy-[1,1'-biphenyl]-4-yl}carbamoyl) cyclopent-1-ene-1-carboxylic acid) according to formula (I)

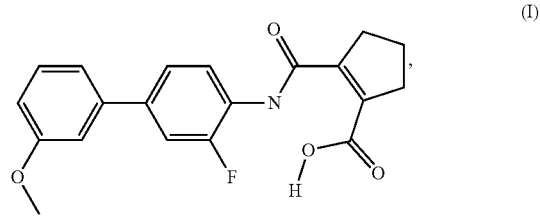 [SMILES: COc1cccc(-c2ccc(NC(=O)C3=C(C(=O)O)CCC3)c(F)c2)c1]

or salts thereof or solvates of the compound of formula (I) or the salts thereof for use as a medicament in a patient in need thereof, wherein said compound or salts thereof or the solvates of the said compound and the salts thereof is initially administered to said patient in an initial daily dose of 14-130 µmol of the active moiety of the compound of formula (I) for a period of minimum 5 and maximum 10 days and is thereafter administered in a second dose that is at 1.5 to 8.0-fold higher than the said initial daily dose.

A compound according formula (I) may be called "vidofludimus" as international non-proprietary name.

In the context of the present invention "administration of a" or "administering a" or any other grammatical loon thereof means that the present compound of formula (I) is administered in the form of a pharmaceutical composition, optionally comprising a pharmaceutically acceptable carrier.

Pharmaceutically acceptable carriers or excipients include diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), thickening agents (e.g. methylcellulose or hydroxyethylcellulose), sweetening agents (e.g. sorbitol, saccharin, aspartame, acesulfame), flavoring agents (e.g. peppermint, lemon oils, butterscotch, etc), humectants (e.g. propylene, glycol, glycerol, sorbitol). Other suitable pharmaceutically acceptable excipients are inter alia described in Remington's Pharmaceutical Sciences, 15$^{th}$ Ed., Mack Publishing Co., New Jersey (1991) and Bauer et al., Pharmazeutische Technologie, 5$^{th}$ Ed., Govi-Verlag Frankfurt (1997).

The person skilled in the art knows suitable formulations for vidofludimus. Vidofludimus may be formulated as e.g. tablets, capsules, granules, powders, sachets, reconstitutable powders, dry powder inhalers and chewables. Such solid formulations may comprise excipients and other ingredients in suitable amounts. Such solid formulations may contain e.g. cellulose, cellulose microcrystalline, polyvidon in particular FB polyvidon, magnesium stearate and the like.

The person skilled in the art will readily be able to choose suitable pharmaceutically acceptable carriers or excipients, depending, e.g., on the formulation and administration route of the pharmaceutical composition.

It is to be understood that a pharmaceutical composition comprising the present compound is for use to be administered to a human patient. The term "administering" in all of its grammatical forms means administration of a sole therapeutic agent or in combination with another therapeutic agent. It is thus envisaged that the pharmaceutical composition of the present invention are employed in co-therapy approaches, i.e. in co-administration with other medicaments or drugs and/or any other therapeutic agent which might be beneficial in the context of the methods of the present invention.

In some embodiments of the invention, said first dose is not therapeutically active, i.e. it is a sub-therapeutic dose, which means doses lower than 20 mg of vidofludimus which is equivalent to 56 µmol of the compound according to formula (I). Without being strictly bound, for the purpose of the present invention a dose of 56 µmol or lower is held to be sub-therapeutic.

Such "first dose" being sub-therapeutic may comprise more than one dose. Thus, for instance, two sub-therapeutic doses may be administered subsequently.

In a preferred embodiment of the present invention the second dose is therapeutically active.

In case that more than one sub-therapeutic dose had been administered, said therapeutically active dose may be the third or fourth dose, but in any case the first therapeutically active dose after one or more sub-therapeutic doses. The first therapeutically active dose may be called the subsequent dose hereinafter but is meant to be the first dose that is intended to be therapeutically active. The therapeutically active dose may be administered for an unterminated period of time, e.g. for one or more years.

Subject matter of the present invention is further a method of prevention and/or treatment of a patient in need thereof, wherein a compound that is 2-({3-fluoro-3'-methoxy-[1,1'-biphenyl]-4-yl}carbamoyl)cyclopent-1-ene-1-carboxylic acid) according to formula (I)

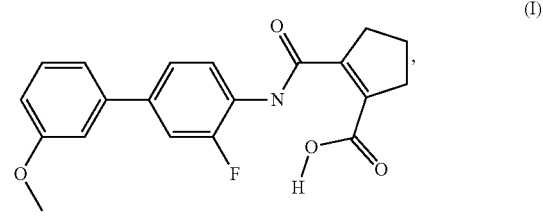 [SMILES: COc1cccc(-c2ccc(NC(=O)C3=C(C(=O)O)CCC3)c(F)c2)c1]

(I)

or salts thereof or solvates of the compound of formula (I) or the salts thereof is initially administered to said patient in an initial daily dose of 14-100 µmol of the active moiety of the compound for a period of minimum 5 and maximum 10 days and is thereafter administered in a subsequent, e.g. second, dose in case of only one pre-treatment dose, wherein said subsequent dose is 28-200 µmol of the active moiety of the compound daily. In one embodiment the subsequent, e.g. second dose is at 1.5 to 4.0 higher than the initial daily dose.

Subject matter of the present invention is further the use of a compound that is 2-({3-fluoro-3'-methoxy-[1,1'-biphenyl]-4-yl}carbamoyl)cyclopent-1-ene-1-carboxylic acid) according to formula (I)

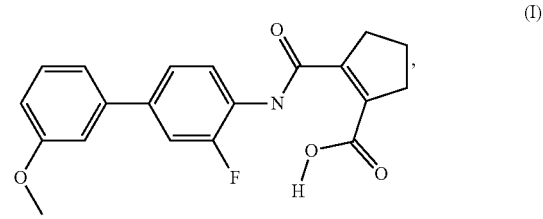 [SMILES: COc1cccc(-c2ccc(NC(=O)C3=C(C(=O)O)CCC3)c(F)c2)c1]

(I)

or salts thereof or solvates of the compound of formula (I) or the salts thereof for the preparation of a medicament in a method of prevention and/or treatment of a patient in need thereof, wherein the compound or salts thereof or the solvates of the compound (I) and the salts thereof is initially administered to said patient in an initial daily dose of 14-100 µmol of the active moiety of the compound (I) for a period of minimum 5 and maximum 10 days, and is thereafter administered in a subsequent, e.g. second, dose that is at 1.8 to 2.2-fold higher than the initial daily dose.

Suitable salts of the compound according to formula (I) can be formed with the free acid 2-({3-fluoro-3'-methoxy-[1,1'-biphenyl]-4-yl}carbamoyl)cyclopent-1-ene-1-carboxylic acid) and an inorganic or organic acids or bases. Examples of such salts are, for example, alkali metal salts, in particular sodium and potassium salts, or ammonium salts.

A solvate of 2-({3-fluoro-3'-methoxy-[1,1'-biphenyl]-4yl}carbamoyl)cyclopent-1-ene-1-carboxylic acid) may be selected from the group comprising protic solvent such as alcohols and water. Said alcohols may be selected from the group comprising ethanol, n-propanol, iso-propanol and butanol.

A solvate of the above-mentioned salts maybe selected from the group comprising water, ethanol, n-propanol, iso-propanol and butanol.

In one embodiment of the invention said first dose of the active moiety of the compound (I) is 14-130 μmol, preferably 14-64 μmol of the active moiety of the compound (I), more preferred 53-64 μmol of the active moiety of the compound (I).

In one embodiment of the invention said subsequent, e.g. second, dose is 1.5 to 8.0-fold higher than the initial daily dose (pre-treatment dose), preferably 1.5 to 4-fold higher than the initial daily dose, more preferably 1.5-3-fold higher than the initial daily dose, even more preferably 1.5-2.5-fold higher than the initial daily dose, most preferred two-fold higher than the initial daily dose.

In one embodiment of the invention said subsequent, e.g. second, dose is 28-200 μmol of the active moiety of the compound (I) daily in its use for a method of prevention and/or treatment of a patient on need thereof. Said subsequent, e.g. second, dose is preferably 56-200 μmol of the active moiety of the compound daily in its use in a method of treatment of a patient on need thereof, more preferably 63-140 μmol of the active moiety of the compound (I) daily in its use in a method of treatment of a patient in need thereof, even more preferably 100-140 μmol of the active moiety of the compound (I) daily in its use in a method of prevention and/or treatment of a patient in need thereof.

In one embodiment of the invention said patient that is in need of said method of prevention and/or treatment suffers from a chronic inflammatory and/or autoimmune disease. In one preferred embodiment of the invention said patient suffers from a chronic inflammatory and/or autoimmune disease selected from the group consisting of rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma or athropathy. In one embodiment of the invention said patient suffers from a chronic inflammatory and/or autoimmune disease selected from the group comprising graft versus host and host versus graft reactions, rheumatoid arthritis, psoriatic arthritis, multiple sclerosis, lupus erythematosus, lupus nephritis, inflammatory bowel disease, type 1 diabetes, autoimmune hepatitis, primary sclerosing cholangitis, primary biliary cholangitis and psoriasis. In one particular embodiment of the invention said patient suffers from inflammatory bowel disease, in particular ulcerative colitis and Crohn's disease.

In one embodiment of the invention the compound 2-({3-fluoro-3'-methoxy-[1,1'-biphenyl]-4-yl}carbamoyl)cyclopent-1-ene-1-carboxylic acid) or a solvate thereof is administered. Said solvate may be selected from the group comprising water, ethanol, n-propanol, iso-propanol and butanol.

In another embodiment of the invention the calcium salt of the compound that is Ca [2-({3-fluoro-3'-methoxy-[1,1'-biphenyl]-4-yl}carbamoyl)cyclopent-1-ene-1-carboxylic acid)](Example 2, CAS No. 1354012-90-0) or a solvate thereof is administered. Said solvate may be selected from the group comprising water, ethanol, n-propanol, iso-propanol and butanol.

In one embodiment of the invention the first daily dose is 63.3 μmol and the subsequent dose is 126.6 μmol.

In one embodiment of the invention the first daily dose has a duration between 5 and 10 days, in one particular embodiment the duration is 5, 6, 7, 8, or 9 days, in one particular embodiment a duration of 7 days.

In one particular embodiment the duration of the second daily dose is at least one month, or at least 6 months. The phase of the second dose may be unlimited or as long as the patient is in need thereof.

In one embodiment of the invention the solvate is an ethanol solvate or a dehydrate of the compound that is 2-({3-fluoro-3'-methoxy-[1,1'-biphenyl]-4-yl}carbamoyl) cyclopent-1-ene-1-carboxylic acid) according to formula (I) or salts thereof

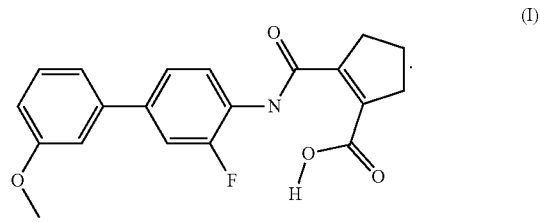 [SMILES: COc1cccc(-c2ccc(NC(=O)C3=C(C(=O)O)CCC3)c(F)c2)c1]

(I)

In the following table μmol of the active moiety of the compound is converted into mg of the free acid of a compound of formula (I) and the calcium salt dihydrate of the compound of formula (I):

TABLE I

| mg Ca (I)$_2$ × 2 H$_2$O | mg (I) | μmol (I) |
|---|---|---|
| 5.52 | 5 | 14.07 |
| 11.04 | 10 | 28.14 |
| 16.56 | 15 | 42.21 |
| 22.08 | 20 | 56.28 |
| 24.85 | 22.5 | 63.32 |
| 33.13 | 30 | 84.42 |
| 49.69 | 45 | 126.63 |
| 55.21 | 50 | 140.70 |
| 77.30 | 70 | 196.98 |

With the above context, specific embodiments of the invention are represented by the below consecutively numbered embodiments:

1. A compound that is 2-({3-fluoro-3'-methoxy-[1,1'-biphenyl]-4-yl}carbamoyl)cyclopent-1-ene-1-carboxylic acid) according to formula (I)

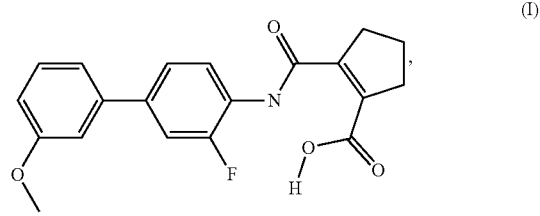 [SMILES: COc1cccc(-c2ccc(NC(=O)C3=C(C(=O)O)CCC3)c(F)c2)c1]

(I)

or salts thereof or solvates of the compound (I) or the salts thereof for use as a medicament in a patient in need thereof, wherein said compound or salts thereof or solvates of the said compound and the salts thereof is initially administered to said patient in an initial daily dose of 14-130 μmol of the active moiety of the said compound for a period of minimum 5 and maximum 10 days, and is thereafter administered in a second dose that is 1.5 to 8.0-fold higher than said initial daily dose.

2. A compound that is 2-({3-fluoro-3'-methoxy-[1,1'-biphenyl]-4-yl}carbamoyl)cyclopent-1-ene-1-carboxylic acid) or salts thereof or solvates of said compound or salts thereof for use as a medicament in a patient in need thereof according to embodiment 1, wherein said second dose is 28-200 µmol of the active moiety of the compound daily.
3. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to embodiment 1 or 2, wherein said patient suffers from a chronic inflammatory and/or autoimmune disease.
4. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of embodiments 1 to 3, wherein said patient suffers from a chronic inflammatory and/or autoimmune disease selected from the group consisting of rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma or athropathy.
5. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of the embodiments 1 to 4, wherein said patient suffers from a chronic inflammatory and/or autoimmune disease selected from the group comprising graft versus host and host versus graft reactions, rheumatoid arthritis, multiple sclerosis, lupus erythematosus, inflammatory bowel disease, type 1 diabetes and psoriasis.
6. A compound that is 2-({3-fluoro-3'-methoxy-[1,1'-biphenyl]-4-yl}carbamoyl)cyclopent-1-ene-1-carboxylic acid) or salts thereof or solvates of the compound or the salts thereof for use as a medicament in a patient in need thereof according to any of embodiments 1 to 5, wherein said patient suffers from inflammatory bowel disease, in particular ulcerative colitis and Crohn's disease.
7. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of the embodiments 1 to 6, wherein the compound 2-({3-fluoro-3'-methoxy-[1,1'-biphenyl]-4-yl}carbamoyl)cyclopent-1-ene-1-carboxylic acid) or a solvate thereof is administered.
8. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of the embodiments 1 to 6, wherein the calcium salt of the compound or a solvate thereof is administered.
9. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of the embodiments 1 to 8, wherein the first daily dose is 63.3 µmol and the subsequent dose is 126.6 µmol.
10. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to the embodiments 1 to 9, wherein the first daily dose is 7 days.
11. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for use as a medicament in a patient in need thereof according to any of the embodiments 1 to 10, wherein the solvate is an ethanol solvate or a dehydrate.
12. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof, wherein said compound or salts thereof or solvates of the said compound and the salts thereof is initially administered to said patient in an initial daily dose of 14-130 µmol of the active moiety of the said compound for a period of minimum 5 and maximum 10 days, and is thereafter administered in a second dose that is 1.5 to 8.0-fold higher than said initial daily dose.
13. A compound that is 2-({3-fluoro-3'-methoxy-[1,1'-biphenyl]-4-yl}carbamoyl)cyclopent-1-ene-1-carboxylic acid) or salts thereof or solvates of said compound or salts thereof for the prevention and/or treatment of a disease in a patient in need thereof according to embodiment 12, wherein said second dose is 28-200 µmol of the active moiety of the compound daily.
14. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to embodiment 12 or 13, wherein said patient suffers from a chronic inflammatory and/or autoimmune disease.
15. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of embodiments 12 to 14, wherein said patient suffers from a chronic inflammatory and/or autoimmune disease selected from the group consisting of rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma or athropathy.
16. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of the embodiments 12 to 15, wherein said patient suffers from a chronic inflammatory and/or autoimmune disease selected from the group comprising graft versus host and host versus graft reactions, rheumatoid arthritis, multiple sclerosis, lupus erythematosus, inflammatory bowel disease, type 1 diabetes and psoriasis.

17. A compound that is 2-({3-fluoro-3'-methoxy-[1,1'-biphenyl]-4-yl}carbamoyl)cyclopent-1-ene-1-carboxylic acid) or salts thereof or solvates of the compound or the salts thereof for the prevention and/or treatment of a disease in a patient in need thereof according to any of the embodiments 12 to 16, wherein said patient suffers from inflammatory bowel disease, in particular ulcerative colitis and Crohn's disease.

18. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of the embodiments 12 to 17, wherein the compound 2-({3-fluoro-3'-methoxy-[1,1'-biphenyl]-4-yl}carbamoyl)cyclopent-1-ene-1-carboxylic acid) or a solvate thereof is administered to said patient.

19. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of the embodiments 12 to 18, wherein the calcium salt of the compound or a solvate thereof is administered to said patient.

20. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of the embodiments 12 to 19, wherein the first daily dose is 63.3 µmol and the subsequent dose is 126.6 µmol.

21. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof thereof according to the embodiments 12 to 20, wherein the first daily dose is 7 days.

22. A compound that is 2-({3-fluoro-3'-methoxy-[1,1'-biphenyl]-4-yl}carbamoyl)cyclopent-1-ene-1-carboxylic acid) or salts thereof or solvates of the said compound or the salts thereof for the prevention and/or treatment of a disease in a patient in need thereof according to any of the embodiments 12 to 21, wherein the solvate is an ethanol solvate or a dehydrate.

Abbreviations/Definitions

DHODH—dihydroorotate dehydrogenase
RBC—red blood cell count
IMU-838=vidofludimus-calcium As used throughout the Examples section the terms "mean value" and "median value", respectively, of a data sample are well-known terms in statistics. The use of these terms in the present application complies with the corresponding definitions in general statistics textbooks. Generally, the mean value is calculated by addition of several quantities and dividing the sum by the number of said quantities. The median value is the value separating the higher half from the lower half of a data sample.

FIGURE DESCRIPTION

FIG. 1: FIG. 1 shows urate concentrations in the blood of healthy volunteers at different time points receiving a single dose of 30 mg of IMU-838.

Figure 2A:
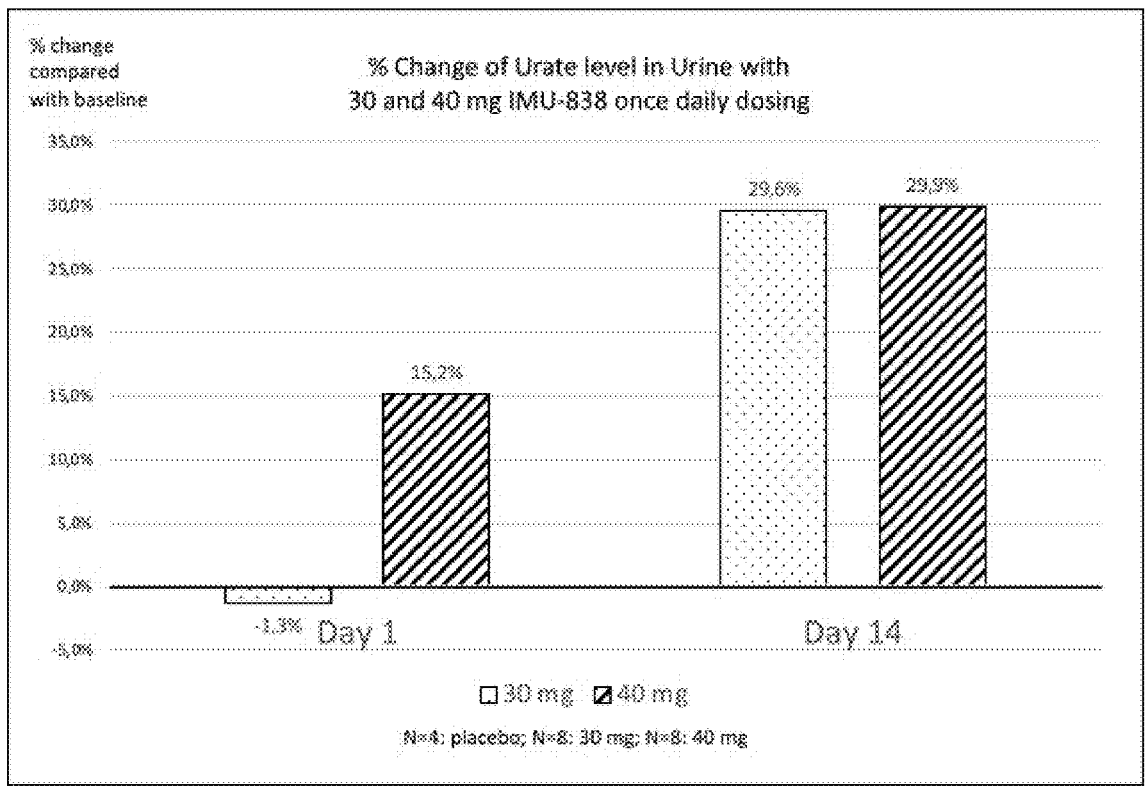

FIG. 2a: FIG. 2a shows the median urate levels in urine with 30 mg and 40 mg IMU-838 treatment at three time points: baseline (24 hours before treatment), at day 1 of the treatment and at day 14 of the treatment. The figure shows the mean values of uric acid for each group. Each group consists of 16 patients with 12 individuals receiving active drug IMU-838 (either 30 or 40 mg per day) and 4 patients receiving placebo.

Figure 2B:
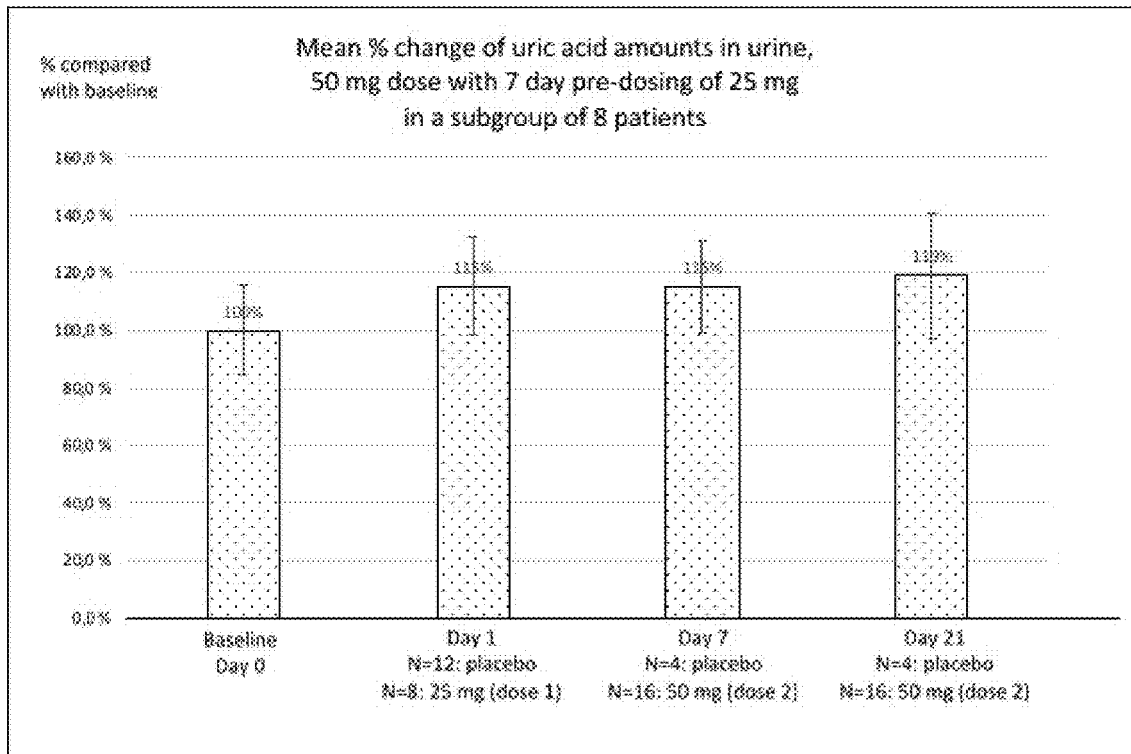

FIG. 2b: FIG. 2b shows the median change in % of uric acid levels in the urine of together 20 healthy volunteers. 8 individuals were treated with 25 mg for 7 days, followed by 14 day treatment with a dose of 50 mg once daily. Another 8 volunteers were treated with placebo (dose 1=0 mg) for 7 days followed by treatment of 50 mg IMU-838. 4 volunteers received placebo for the whole time. FIG. 2c shows the mean change of uric acid amount in urine at four time points in % change.

EXAMPLES

Example 1

Effect of IMU-838 (vidofludimus-calcium) on Uric Acid Levels in Urine

During the IMU-838 (vidofludimus-calcium) phase I SAD study (Immunic study number P1-IMU-838-SAD), urine was collected from all volunteers and tested with respect to the amount of clinical relevant anions, including urate and oxalate. In addition, formation of anion crystals in the urine was measured. In this study, IMU-838 was tested as a single dose applied to male healthy volunteers. Five different dose regimens were tested which covered four different doses of IMU-838: 10 mg, 20 mg, 30 mg and 40 mg of IMU-838 in fastened patients, which means no food intake 10 hours prior to the treatment and two hours after dose application. In addition, one dose group received 10 mg of IMU-838 in fed state which means that the 10 mg dose was applied after a high-fat breakfast. Each group consisted of six healthy volunteers, except for the 40 mg dose group with only five volunteers. The maximum plasma concentrations ($c_{max}$) increased from 1.5772 µg/mL for fastened volunteers with 10 mg IMU-838 dose to 7.8561 µg/mL for patients who received 40 mg dose of IMU-838.

Patients with the highest dose of 40 mg showed a higher increase of uric acid amounts in urine of 50.1% compared with the patients who received 10 mg of IMU-838 which had a mean increase of 22.5%. This is shown in Table 2. The pre-dose value was derived from urine collected 24 hours before application of IMU-838 tablets. The post dose value was obtained by collecting 24 hours urine starting 4 hours after intake of IMU-838.

TABLE 2

Uric acid levels in 24 h collected urine in P1-IMU-838-SAD study - comparison of high dose (40 mg) with low dose (10 mg).

| Uric acid (mg/24 h) | 10 mg fasted N = 6 | 40 mg fasted N = 5 |
|---|---|---|
| Pre dose (−24 h to 0) | 520 | 489[a] |
| Post dose (4 to 28 h) | 637 | 734 |

TABLE 2-continued

Uric acid levels in 24 h collected urine in P1-IMU-838-SAD study - comparison of high dose (40 mg) with low dose (10 mg).

| Uric acid (mg/24 h) | 10 mg fasted N = 6 | 40 mg fasted N = 5 |
|---|---|---|
| Increase of mean uric acid levels | 117 (22.5%) | 245 (50.1%) |

<sup>a</sup>N = 4; N = number of subjects

An increased concentration of urate in urine was found in all patients, however not leading to increase of RBC (red blood cell count) in urine at the doses tested.

Treatment of humans with IMU-838 leads to dose dependent increase of urate excretion through the urine and thus to formation of urate (micro)crystals. At the doses up to 40 mg of IMU-838 no dose limiting side effects like hematuria occurred.

In this example, also the time dependent change of uric acid levels in blood were tested. At 30 mg single dose, the plasma levels of uric acid drop after 4 hours to a minimum and go back to baseline levels after 96 hours. This is shown in FIG. 2.

Example 2

Effect of IMU-838 (vidofludimus-calcium) on Uric Acid Levels in Urine After Multiple Dosing without Predosing In a randomized, placebo controlled double blind clinical Phase I MAD trial (Immunic study number P1-IMU-838-MAD), IMU-838 was applied to healthy volunteers for 14 days in order to test the effects of IMU-838 on safety and biomarkers for repeated once daily doses over 14 days. In the first part of this study, 12 individuals were treated with 30 mg of IMU-838, 12 individuals were treated with 40 mg of IMU-838 and 8 individuals received placebo (4 individuals in each group). For all 32 individuals, urate levels in the urine was quantified in three periods of 24 hour urine collection. The first collection was at pre-dose (day 0). The second urine collection started four hours after intake of the first dose (day 1, 4 hours to 28 hours). The third collection of urine was performed on the last day of the 14 day treatment cycle (day 14, 4 hours to 28 hours). The amounts of uric acid at those timepoints is depicted in FIG. 2a.

Result: Surprisingly, the increase of uric acid measured in the urine was not related to the applied doses in a linear fashion. In the 30 mg dose there was no increase at day one of the intake of IMU-838 but a 29% increase from 605.9 mg to 686.2 mg (FIG. 2a) after 14 days of daily treatment. The amount of uric acid in the 40 mg group jumped by already 15.2% from 541.4 mg to 620.3 at the first day (4-28 hours after intake of 40 mg of IMU-838) and then rising to 699.3 mg at day 14 of the study. Therefore, the increase of uric acid levels was quick at the first day of treatment and only moderate with a slow onset during the next 13 days. In the 40 mg dose group, there was no further increase of the mean levels of uric acid in the urine. The data is shown in FIG. 2a.

Interestingly, despite the fact that the subjects received different doses of IMU-838, the volunteers showed a comparable increase of uric acid of around 30% compared with pre-treatment after the full 14 days treatment time.

We also conclude that the rapid increase of urate in the urine is dose dependent. Doses of 30 mg or lower have a low effect on urate levels at the first day of treatment with IMU-838.

Example 3

Effect of Vidofludimus on Uric Acid Levels in Urine After a Dose-In Phase Before Multiple Dosing Based on the observations on a) dose dependent effect of IMU-838 on urate levels in the urine and formation of small crystals (example 1) and b) the time course and dose dependence of urate level changes in single volunteers (example 2) a new therapeutic treatment scheme was invented. In this example a treatment scheme was applied to a three week clinical phase I trial consisting of two different doses "dose 1" of 25 mg daily dose and "dose 2" of 50 mg daily dose. 8 subjects received a lower dose 1 for 7 days followed by the higher (double) dose 2 for further 14 days, whereas another 8 subjects received placebo for 7 days then followed by treatment with the 50 mg high dose (dose 2). 4 subjects received placebo during the foll three week period. During this study urine was collected at four different timepoints (pre-dose, day 1, day 7, day 14) and analyzed for urate/uric acid levels.

The mean increase in 24 hours urinary urate levels of all 20 patients was 15% from 684.1 mg to 789.5 mg after 1 day of treatment (4-28 hours) including the patients receiving placebo.

Surprisingly, the mean urate levels in the collected urine at the first day of application of dose 2 (day 7 of the full trial) did not increase (789.5 to 789.7 mg), even if 8 of the volunteers were treated with the high dose of 50 mg immediately without receiving dose 1 before. After the full period of three weeks (day 21) the overall increased slightly by 4% from 789.7 mg to 815.9 mg.

Conclusion:

Using a stepwise dosing of IMU-838 with a lower first dose of 25 mg IMU-838 followed by a higher second dose of 50 mg IMU-838 leads to a reduced increase of mean amounts of urate in the urine, in this case to a reduction of the mean urate levels in the timeframe of 4 to 28 hours after intake of 50 mg. Even if the data is diluted with individuals receiving placebo, the effect was clearly seen.

We conclude that starting with a low-dose treatment and then switching to a higher dose can avoid an unwanted fast and or strong immediate excretion of high amounts of uric acid/urate while reaching higher therapeutic levels of IMU-838 when increasing the dose in the second phase. The experiment resulted in an updosing scheme with a lower urate gradient compared with immediate dosing.

Example 4

Clinical Study Comparing Treatment With and Without Pre-treatment Phase

A double-blind clinical study, Placebo controlled, Ascending Dose has been conducted. This study has been reported (Study Number P1-IMU-838-MAD).

The urinary excretion of uric acid increased in all but the 30 mg group after treatment initiation with IMU-838 (vidofludimus-calcium). No dose-dependency was apparent.

Uric acid excretion in urine could be however modified with a pre-treatment period. Pre-treatment with 25 mg IMU-838 for 6 days in subjects receiving 50 mg IMU-838 resulted in a smaller increase in uric acid excreted in urine on Day 0 (the first day of receiving the 50 mg dose) as compared to pre-treatment with placebo (49.5 mg/24 hours vs 86.5 mg/24 hours, respectively, median levels).

| Group | Placebo group/ 50 mg | Pre-dosing group 25 mg/50 mg |
|---|---|---|
| n | 8 | 8 |
| Change in Median (mg/24 h) | 86.5 | 49.5 |

Thus, the superiority of a treatment regimen including a pre-treatment phase in comparison to a treatment without such a pre-treatment phase has been proven.

The invention claimed is:

1. A method of treating multiple sclerosis in a subject in need thereof, the method comprising:
   a) administering to the subject at least one compound each day for 5 to 10 days at an initial daily dose of about 14 µmol to about 130 µmol per day; and thereafter
   b) administering to the subject the at least one compound at a subsequent daily dose,
   wherein the subsequent daily dose is 1.5 to 8-fold higher than the initial daily dose, and
   wherein the at least one compound includes 2-({3-fluoro-3'-methoxy-[1,1'-biphenyl]-4-yl}carbamoyl)cyclopent-1-ene-1-carboxylic acid or a pharmaceutically-acceptable salt or solvate thereof.

2. The method of claim 1, wherein the initial daily dose is about 42 µmol per day.

3. The method of claim 1, wherein the initial daily dose is about 63 µmol per day.

4. The method of claim 1, wherein the subsequent daily dose is 1.5 to 4-fold higher than the initial daily dose.

5. The method of claim 4, wherein the subsequent daily dose is 2-fold higher than the initial daily dose.

6. The method of claim 1, wherein the administering to the subject of the at least one compound at the initial daily dose is for 6-8 days.

7. The method of claim 6, wherein the administering to the subject of the at least one compound at the initial daily dose is for 7 days.

8. The method of claim 1, wherein the at least one compound is 2-({3-fluoro-3'-methoxy-[1,1'-biphenyl]-4-yl}carbamoyl)cyclopent-1-ene-1-carboxylic acid.

9. The method of claim 1, wherein the at least one compound is a calcium salt of 2-({3-fluoro-3'-methoxy-[1,1'-biphenyl]-4-yl}carbamoyl)cyclopent-1-ene-1-carboxylic acid or solvate thereof.

10. The method of claim 9, wherein the at least one compound is a calcium salt of 2-({3-fluoro-3'-methoxy-[1,1'-biphenyl]-4-yl}carbamoyl)cyclopent-1-ene-1-carboxylic acid.

11. The method of claim 9, wherein the at least one compound is a dihydrate of a calcium salt of 2-({3-fluoro-3'-methoxy-[1,1'-biphenyl]-4-yl}carbamoyl)cyclopent-1-ene-1-carboxylic acid.

12. A method of treating multiple sclerosis in a subject in need thereof, the method comprising:
   a) administering to the subject at least one compound selected from the group consisting of 2-({3-fluoro-3'-methoxy-[1,1'-biphenyl]-4-yl}carbamoyl)cyclopent-1-ene-1-carboxylic acid, a pharmaceutically-acceptable salt and a solvate thereof each day for 5 to 10 days at an initial daily dose of about 5 mg to about 45 mg per day; and thereafter
   b) administering to the subject the at least one compound selected from the group consisting of 2-({3-fluoro-3'-methoxy-[1,1'-biphenyl]-4-yl}carbamoyl)cyclopent-1-ene-1-carboxylic acid, a pharmaceutically-acceptable salt and a solvate thereof at a subsequent daily dose,
   wherein the subsequent daily dose is 1.5 to 8-fold higher than the initial daily dose, and
   wherein the initial daily dose and the subsequent daily dose are calculated based on the weight of 2-({3-fluoro-3'-methoxy-[1,1'-biphenyl]-4-yl}carbamoyl)cyclopent-1-ene-1-carboxylic acid.

13. The method of claim 12, wherein the at least one compound is 2-({3-fluoro-3'-methoxy-[1,1'-biphenyl]-4-yl}carbamoyl)cyclopent-1-ene-1-carboxylic acid.

14. The method of claim 12, wherein the at least one compound is a calcium salt of 2-({3-fluoro-3'-methoxy-[1,1'-biphenyl]-4-yl}carbamoyl)cyclopent-1-ene-1-carboxylic acid or solvate thereof.

15. The method of claim 14, wherein the at least one compound is a calcium salt of 2-({3-fluoro-3'-methoxy-[1,1'-biphenyl]-4-yl}carbamoyl)cyclopent-1-ene-1-carboxylic acid.

16. The method of claim 14, wherein the at least one compound is a dihydrate of a calcium salt of 2-({3-fluoro-3'-methoxy-[1,1'-biphenyl]-4-yl}carbamoyl)cyclopent-1-ene-1-carboxylic acid.

17. The method of claim 12, wherein the initial daily dose is about 15 mg per day.

18. The method of claim 12, wherein the initial daily dose is about 22.5 mg per day.

19. The method of claim 12, wherein the subsequent daily dose is 1.5 to 4-fold higher than the initial daily dose.

20. The method of claim 19, wherein the subsequent daily dose is 2-fold higher than the initial daily dose.

21. The method of claim 12, wherein the administering to the subject of the at least one compound at the initial daily dose is for 6-8 days.

22. The method of claim 21, wherein the administering to the subject of the at least one compound at the initial daily dose is for 7 days.

23. A method of treating multiple sclerosis in a subject in need thereof, the method comprising:
   a) administering to the subject at least one compound each day for 7 days at an initial daily dose; and thereafter
   b) administering to the subject the at least one compound at a subsequent daily dose,
   wherein the initial daily dose is about 42 µmol per day to about 63 µmol per day,
   wherein the subsequent daily dose is about 84 µmol per day about 126.6 µmol per day, and
   wherein the at least one compound includes 2-({3-fluoro-3'-methoxy-[1,1'-biphenyl]-4-yl}carbamoyl)cyclopent-1-ene-1-carboxylic acid or a pharmaceutically-acceptable salt or solvate thereof.

24. The method of treating multiple sclerosis of claim 23, wherein the initial daily dose is about 42 µmol per day and wherein the subsequent daily dose is about 84 µmol per day.

25. The method of treating multiple sclerosis of claim 23, wherein the initial daily dose is about 63 µmol per day and wherein the subsequent daily dose is about 126.6 µmol per day.

26. The method of claim 23, wherein the at least one compound is 2-({3-fluoro-3'-methoxy-[1,1'-biphenyl]-4-yl}carbamoyl)cyclopent-1-ene-1-carboxylic acid.

27. The method of claim 23, wherein the at least one compound is a calcium salt of 2-({3-fluoro-3'-methoxy-[1,1'-biphenyl]-4-yl}carbamoyl)cyclopent-1-ene-1-carboxylic acid or solvate thereof.

28. The method of claim 27, wherein the at least one compound is a calcium salt of 2-({3-fluoro-3'-methoxy-[1,1'-biphenyl]-4-yl}carbamoyl)cyclopent-1-ene-1-carboxylic acid.

29. The method of claim 27, wherein the at least one compound is a dihydrate of a calcium salt of 2-({3-fluoro-3'-methoxy-[1,1'-biphenyl]-4-yl}carbamoyl)cyclopent-1-ene-1-carboxylic acid.

30. A method of treating multiple sclerosis in a subject in need thereof, the method comprising:
   a) administering to the subject at least one calcium salt of 2-({3-fluoro-3'-methoxy-[1,1'-biphenyl]-4-yl}carbamoyl)cyclopent-1-ene-1-carboxylic acid or solvate thereof each day for 7 days at an initial daily dose; and thereafter
   b) administering to the subject the at least one calcium salt of 2-({3-fluoro-3'-methoxy-[1,1'-biphenyl]-4-yl}carbamoyl)cyclopent-1-ene-1-carboxylic acid or solvate thereof at a subsequent daily dose,
   wherein the initial daily dose is about 15 mg per day to about 22.5 mg per day,
   wherein the subsequent daily dose is about 30 mg per day to about 45 mg per day, and
   wherein the initial daily dose and the subsequent daily dose are calculated based on the weight of 2-({3-fluoro-3'-methoxy-[1,1'-biphenyl]-4-yl}carbamoyl)cyclopent-1-ene-1-carboxylic acid.

31. The method of treating multiple sclerosis of claim 22, wherein the initial daily dose is about 15 mg per day and wherein the subsequent daily dose is about 30 mg per day.

32. The method of treating multiple sclerosis of claim 22, wherein the initial daily dose is about 22.5 mg per day and wherein the subsequent daily dose is about 45 mg per day.

33. The method of claim 30, wherein the at least one compound is a calcium salt of 2-({3-fluoro-3'-methoxy-[1,1'-biphenyl]-4-yl}carbamoyl)cyclopent-1-ene-1-carboxylic acid.

34. The method of claim 30, wherein the at least one compound is a dihydrate of a calcium salt of 2-({3-fluoro-3'-methoxy-[1,1'-biphenyl]-4-yl}carbamoyl)cyclopent-1-ene-1-carboxylic acid.

\* \* \* \* \*